LIQUID SUPPLY SYSTEM AND PUMP CONTROL THEREFOR

Original Filed July 28, 1966 2 Sheets-Sheet 1

INVENTOR.
Robert D East
BY Austin A. Webb
ATTORNEY.

LIQUID SUPPLY SYSTEM AND PUMP CONTROL THEREFOR
Original Filed July 28, 1966 2 Sheets-Sheet 2
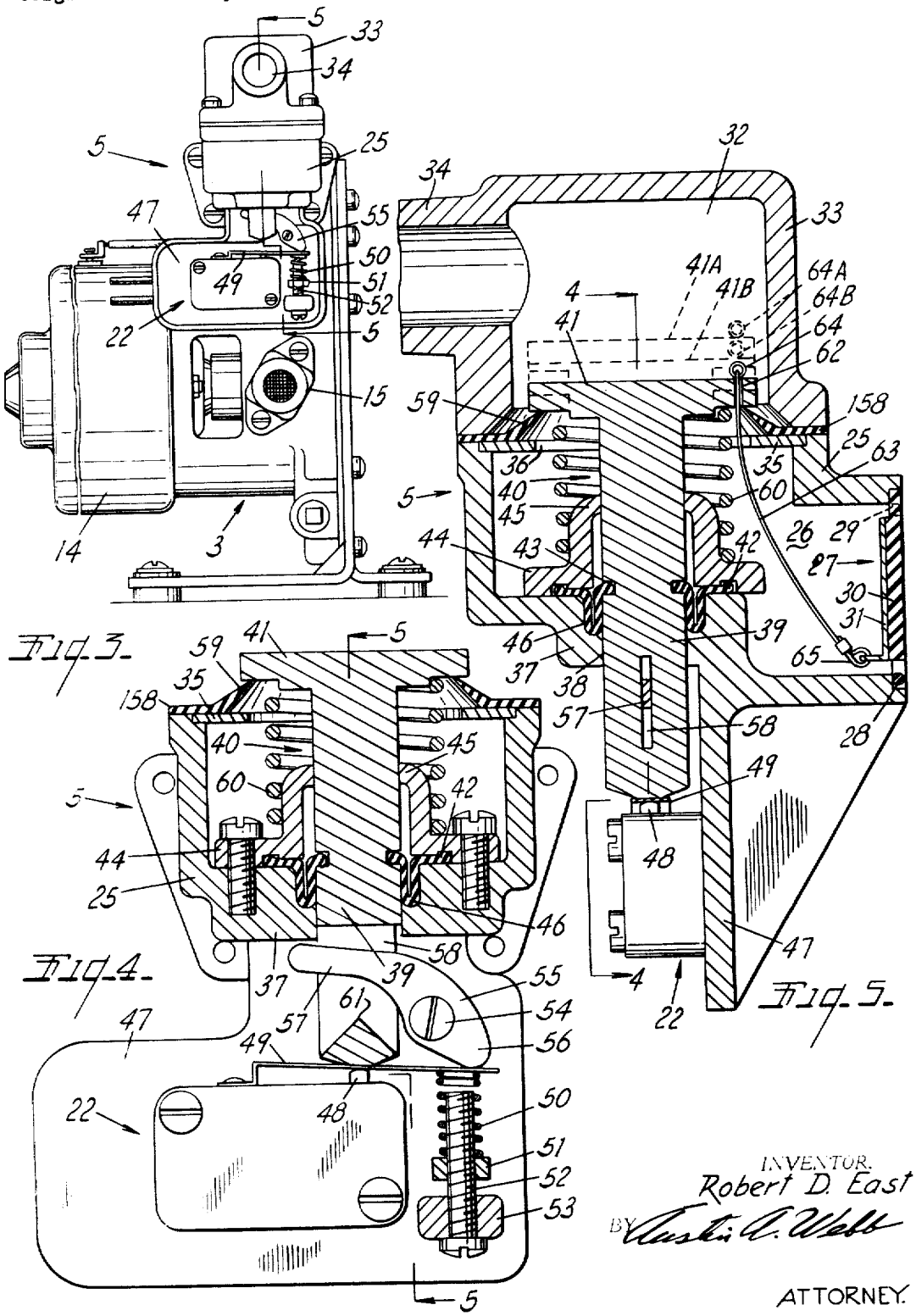
INVENTOR.
Robert D. East
BY Austin A. Webb
ATTORNEY.

United States Patent Office

Re. 26,678
Reissued Oct. 7, 1969

26,678

LIQUID SUPPLY SYSTEM AND PUMP CONTROL THEREFOR

Robert D. East, Galesburg, Mich., assignor to General Gas Light Company, Kalamazoo, Mich.

Original No. 3,376,821, dated Apr. 9, 1968, Ser. No. 568,581, July 28, 1966. Application for reissue Apr. 18, 1968, Ser. No. 753,801
Int. Cl. F04b *49/02*; F04d *15/02*; H01h *13/56*
U.S. Cl. 103—25 23 Claims

Matter enclosed in heavy brackets [ ] appears in the original patent but forms no part of this reissue specification; matter printed in italics indicates the additions made by reissue.

*ABSTRACT OF THE DISCLOSURE*

*A housing attachable to a horizontal discharge from a pump defines a flow passage inwardly and upwardly to an outlet, with a flexible gasket defining a circular opening in the upwardly directed part of the passage. A check valve in the housing closes against the discharge of the pump. A valvelike control disc seats against the top of the gasket and has a stem depending through the bottom of the flow passage, and is spring biased upwardly. The stem actuates a three position switch, connectable to the pump motor to energize the motor in an intermediate position when pressure differential on the disc partially counterbalances its spring bias, and to deenergize the motor at alternate top and bottom positions when lack of liquid flow eliminates pressure differential, or back pressure due to closing the outlet fully overcomes the spring. A flexible connection between the disc and the check valve holds the check valve open in the fully raised position of the disc.*

This invention relates to improvements in liquid supply system and for pump control therefor. The principal objects of this invention are:

First, to provide a liquid supply system, particularly for mobile vehicles, which utilizes a centrifugal pump with a sensitive control system capable of starting the pump upon creation of a demand for water, and keeping the pump running at very low demand rates, while still being capable of automatically shutting off the pump either upon elimination of demand or exhaustion of the supply of water to the pump.

Second, to provide a water supply system for mobile vehicles which includes a centrifugal pump with a demand responsive control, and in which the pump is automatically reprimed after being stopped due to exhaustion of the water supply to the pump, followed by restoration of the water supply and restarting of the pump.

Third, to provide a water supply system for mobile vehicles which utilizes a centrifugal pump and a demand responsive control that will shut off the motor upon elimination of demand, or exhaustion of water supply, or upon mechanical failure of the pump.

Fourth, to provide a water supply system for mobile vehicles which utilizes a centrifugal pump that can be positioned at various levels including a level somewhat above the bottom the supply tank, and still be automatically or self primed upon restoration of a minimum amount of water to the tank.

Fifth, to provide a demand sensitive control for a pump which is responsive to very small demands, and also capable of shutting off the pump upon exhaustion of the supply to the pump, while conditioning the pump to be self priming upon restoration of the water supply and restarting of the pump.

Sixth, to provide a demand responsive control for a pump which is sensitive to very small demands, and also capable of shutting off the pump in response to lack of output pressure due either to lack of supply to the pump or mechanical failure of the pump.

Other objects and advantages of the invention will be apparent from a consideration of the following description and claims. The drawings of which there are two sheets illustrate a highly practical form of the liquid supply system and its control, and one modified portion of the control, particularly adapted for the water system of a mobile vehicle.

FIG. 3 is a fragmentary enlarged side elevational view of the pump and control.

FIG. 4 is a fragmentary vertical cross sectional view through a portion of the control for the water system taken along the plane of the broken line 4—4 in FIG. 5.

FIG. 5 is a fragmentary vertical cross sectional view through the control taken along the plane of broken line 5—5 in FIGS. 3 and 4.

Figure 1:
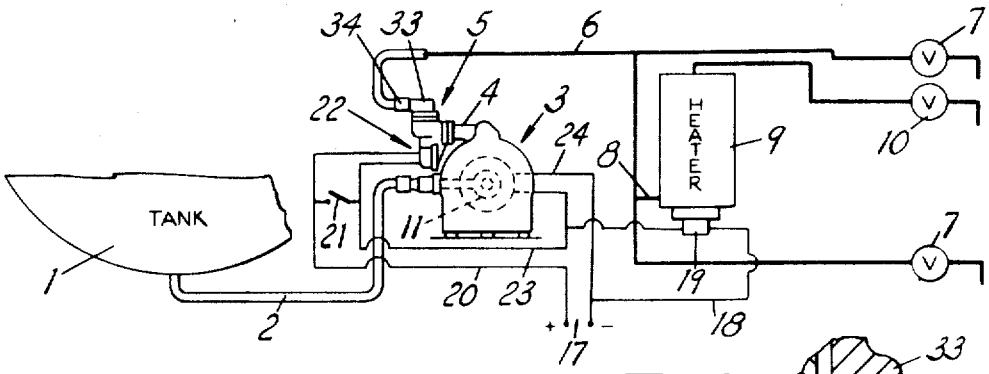
FIG. 1 is a conventional view schematically illustrating the liquid supply system and the electrical circuits associated therewith.
Figure 2:
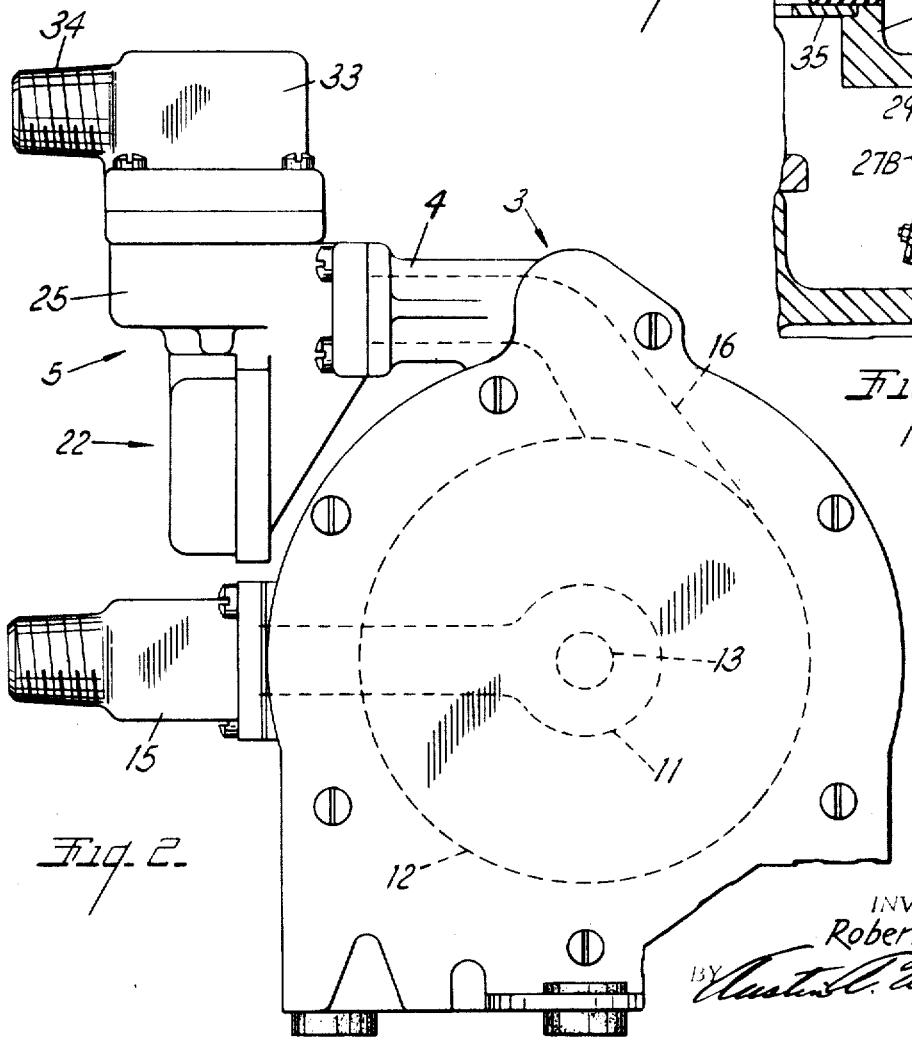
FIG. 2 is a fragmentary enlarged elevational view of the pump and control of the system.

Mobile vehicles such as boats and house trailers are now commonly supplied and equipped with complete water systems in which water from a storage tank is pumped on demand to an outlet valve or faucet. These systems may include branch pipes directed to and from water heaters and because of the limited space and available energy, water heaters have been developed to respond automatically to demand or flow of water therethrough. A variety of electrically driven pumps having controls responsive to demand are also available but these have generally been positive displacement pumps which are inherently relatively noisy. The present system and control permits the use of quiet centrifugal pumps having the operational advantages set forth in the objects above.

The drawings illustrate the water system having a supply tank indicated at 1 and connected near its bottom by a conductor pipe 2 to the inlet of a pump generally indicated at 3. The outlet of the pump indicated at 4 is directed through a portion of the control of the invention indicated generally at 5 to an outlet or delivery pipe 6 extending to cold water faucet valves 7 with a branch pipe 8 delivering to a heater 9. The output from the heater is directed to a hot water faucet valve 10. The components of the supply system may be mounted as is convenient within the particular vehicle concerned but attention is directed to the fact that the central inlet 11 of the pump may be located some distance above the bottom of the tank 1.

The pump 3 is of the centrifugal type having an impeller, not illustrated, which is rotatably driven in the pump chamber 12 by the shaft 13 of an electric motor 14. The inlet to the pump chamber is connected to the inlet fitting 15 while the outlet extends tangentially as at 16 to the outlet connection 4. Pumps and driving motors of this type are well known and so are not described in greater detail.

The electrical system consists of a suitable source of energy 17 connected through the conductor 18 to the control 19 for the water heater. Another conductor 20 extends to a manually operable restart switch 21 which can be located in any convenient position and which is further connected in parallel relation with the automatic switch generally indicated at 22. Either switch 21 or 22 is adapted to complete a circuit to the conductor 23 which extends to the motor with a return conductor 24 to the source 17.

Considering the control 5 and switch 22 in greater detail, attention is directed to FIGS. 4 and 5 where the control 5 is shown to include a control housing 25 which is secured to the outlet end 4 of the pump and which forms an inlet chamber 26 having an inlet opening in its side registering with the outlet 4 of the pump. A check valve generally indicated at 27 is positioned between the pump outlet and the inlet chamber to seat by back pressure against return flow to the pump. In the particular example illustrated the wall of the housing forming the opening that communicates with the pump is recessed to receive a generally circular gasket 28 in clamped relation between the opposed faces of the pump outlet and the housing. A narrow flexible neck 29 at the top of the gasket connects to a central circular flap 30 adapted to seat over the outlet 4 from the pump. A metallic backing plate 31 stiffens the check valve flap against collapse into the pump outlet.

The upper side of the housing 25 is open and communicates with a flow passage 32 defined within a generally rectangular, hollow member 33 having a delivery opening and connection 34 in one side. The member 33 and the top of the housing 25 are desirably rectangular so that the two members may be connected in any of four rotated directions of the outlet 34. A plate 35 having its edges clamped between the housing 25 and the flow passage forming member defines a central hole 36 which may be termed a flow port opening between the inlet chamber and the flow passage 32.

The lower wall 37 of the housing 25 defines a bore 38 centrally below the flow port 36 and through which the stem 39 of a control member is slidably extended. The control member indicated in its entirety by the numeral 40 has a radially enlarged head 41 positioned within the flow passage 32. In order to seal the stem 39 to the wall of the housing a flexible diaphragm 42 has its inner edge secured and sealed in an annular groove 43 in the control member stem with its outer edge clamped between the bottom wall 37 and an annular guide 44 screwed to the inner wall of the housing. The guide 44 has an upwardly offset central portion 45 guidingly engaging the upper portion of the stem 39. The diaphragm 42 has an annular reverse bend or fold 46 which permits free up and down movement of the stem while sealing the stem to the housing.

A depending flange 47 extending below the bottom wall 37 of the housing carries the electric switch 22 below the lower end of the stem 39 of the control member. The switch 22 has an actuating element or push button 48 which normally opens the switch 22 when depressed. A leaf spring 49 secured to the top of the casing of the switch extends over the push button 48 and into the path of a coil spring 50 that is adjustably supported on a nut 51 carried by the screw 52. The screw 52 is supported by a threaded projection 53 from the flange 47. The spring 50 and adjusting nut 51 serve to adjust the resistance to movement of the push button 48 as necessary to compensate for variations in the operating pressure of the switch 22.

Pivotally mounted on the flange 47 by means of the pivot screw 54 is a lever 55 forming a mechanical connection between the control member 40 and the switch 22. The lower right end 56 of the lever as shown in the drawings engages the projecting end of leaf spring 49 while an oppositely projecting arm 57 extends through a slot 58 formed in the lower portion of the stem 39. The lower end of the stem is adapted to contact the spring 49 directly over the push button 48 of the switch.

Positioned between the flow passage forming member 43 and the top of the housing is a gasket 158 having an annular upwardly and inwardly inclined and tapering flange 59 formed thereon. The flange is arranged to seat against the underside of the control member head 41 and substantially close the flow port 36 when the control member and its stem 39 are in extreme lowered switch opening engagement with the control button 48 of the switch. Static or gravity lowering motion of the control member 40 is opposed by a coil spring 60 centered around the guide 45 and bearing against the underside of the head 41. The spring 60 has sufficient force to move the control member to an extreme raised position within the flow passage 32 indicated by dotted lines at 41A when there is no fluid back pressure in the passage 32, as will be described. In this raised or retracted position of the control member into the flow passage the lower edge 61 of the slot 58 engages the arm 57 to rotate the right end of the lever 55 downwardly thus depressing the right end of the spring 49 and simultaneously depressing the push button 48 of the switch. The switch, control member and lever are illustrated in this position in FIG. 3. Engagement of the left arm 57 of the lever with the bottom wall 37 of the housing limits the inward or retracting motion of the control member. When the biasing pressure of the spring 69 on the control member is opposed by a force differential, as will be described presently, the head 41 is depressed to an intermediate position indicated by dotted lines at 41B in FIG. 5 in which position there is an annular opening formed between the flexible annular flange 59 and the bottom of the head 41 through which water may flow to the outlet 34.

In the example of the control illustrated in FIG. 5 there is a mechanical link or connection between the head 41 of the control member and the check valve 27. A small bore 62 formed through the head 41 passes one end of a flexible wire or strand 63 which is anchored to the head by suitable means such as the ring 64. The ring and strand move with the head to the intermediate and extreme retracted positions 64B and 64A respectively and in the extreme retracted position 64A the strand 63 which is connected at its other end to the backing plate 31 of the check valve by the loop 65 holds the check valve in partially open position.

Figure 6:
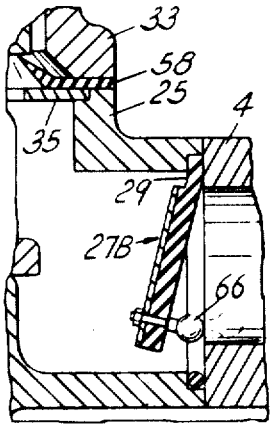
FIG. 6 is a fragmentary vertical cross sectional view corresponding to a portion of FIG. 5 and illustrating a modified form of check valve for the control. The view appears with FIGS. 1 and 2.

The modified form of check valve shown at 27B in FIG. 6 provides a mass or weight 66 secured to the lower portion of the check valve and projecting in offset relation thereto so that the mass will normally hang as illustrated below the suspension point 29 of the flapper check valve and hold the valve partially open unless there is a back pressure in the inlet chamber acting to seat the check valve against the end of the outlet 4 from the pump.

With the foregoing structure the control and water system operate as follows. With the tank 1 filled and any of the valves 7 or 10 open, the manual switch 21 can be closed to initially start the pump and fill the system. The output from the pump will open the check valve 27, fill the inlet chamber 26. Assuming an empty distribution system at the start, the head 41 of the control member will already be raised off of its closure on the flange 59 by the spring 60 so that water will fill the flow passage 32 and the rest of the system. At this point, there will be a back pressure in the system that is approximately equal in chamber 26 and the flow passage 32. However, the greater area of the top of the head 41 exposed to the back pressure creates a force greater than that of the same pressure acting on the bottom of the control member. This pressure created force differential moves the control member, against spring 60, to the intermediate position 41B. In this intermediate position of the control member, both the lower end of the stem 39 and the lever end 56 will be out of contact with the spring 49 and the push button 48 of switch 22 so that switch 22 closes. Manual switch 21 may then be released or opened and the system will continue to function automatically.

So long as any faucet valve is open creating a demand the control member will remain in the intermediate position and the switch 22 will remain closed. However, when the demand is eliminated by closing the faucets 7 and 10, all flow stops. It is a characteristic of centrifugal pump 3 that it output pressure rises sharply under no flow conditions. Raising the pressure raises the force differential on opposite sides of head 41 and pushes the control member downwardly into closed relation or engagement with the flange 59 and simultaneously moves the push button 48, as shown in FIGS. 4 and 5, to open the switch 22 and stop the motor. In this condition the passage 62 which incidentally forms the anchor for the flexible strand 63 functions as a pressure bleed passage so that any pressure differential between the inlet chamber and the flow passage is equalized and the full back pressure in the system acts on the flapper 30 of the check valve to prevent water from flowing back through the pump and into the tank or other low spots such as the connecting pipe 2.

When any faucet valve is later opened, the back pressure in the system and in the flow passage 32 immediately drops so that the combined action of the pressure existing in the inlet chamber and the spring 60 again retracts the control member to intermediate position 41B, and immediately closes switch 22. The pump starts to fill the new demand, and reestablishes the spring balancing force differential on the control member.

It is a particularly desirable feature of the system and the control described that the pump or rather the pump motor will shut down automatically upon elimination of the force differential on the control member 40, for any reason. For example, should the tank run dry eliminating the source of water there can be no fluid pressure or force differential, and under these conditions the spring 60 moves the control member 40 and head 41 to the extreme upper or retracted position 41A. As previously pointed out this motion causes the edge 61 at the bottom of the slot in the control member to activate the lever 55 so that the nose 56 moves the switch 22 to open position. Accordingly, the pump does not continue to run uselessly. The same situation will exist should some mechanical failure in the pump or motor cause the output of the pump to fall below the amount necessary to maintain an operating pressure in the system even though adequate water supply is available. Thus the system will not continue to run without water, or with a faulty pump or motor.

When the motor is stopped by reason of lack of force differential on the control 40, the head 41 moves to open position 41A so water in the pipes 6 and so much of the heater 9 as may be above the level of the outlet 34 drains backwardly through the flow passage 32, inlet chamber 26 and past the check valve 30 to accumulate in the lower portion of the chamber 12 of the centrifugal pump. If a faucet is open the return flow is free, but even with the faucets closed there will be some back-flow, creating a vacuum in high points. There being no substantial back pressure in the system to close the flapper 30 of the check valve, the biasing means such as the mechanical link strand 63 in FIG. 5 or the weight bias 66 in FIG. 6 will hold the check valve open. This feature of permitting back draining into the pump housing permits the pump 3 to be self-priming. Thus should the system be stopped by a lack of water in the tank 1 it can be restarted as soon as any material amount of water is reintroduced into the tank by closing the manual switch 21. The pocket of water collected in the chamber of the centrifugal pump is sufficient to create a suction in the pump for drawing water through the connecting pipe 2 even though the inlet 15 may be some little distance above the level of water in the supply tank. Just how great a level differential may be depends on the construction of the pump and it is desirable to keep the inlet 15 near the bottom of the tank but some differential is permissible and may be required in some installations.

The supply system and control have been illustrated and described in connection with the water supply and distribution system of a mobile vehicle, such as a house trailer or a boat, but the system is not limited to such uses.

What is claimed as new is:

1. A liquid supply system having a supply tank and at least one outlet valve comprising a centrifugal pump having an impeller, and an inlet, a conduit connected between a lower portion of said tank and said inlet to said pump, the inlet to the pump being no higher than the capacity of the pump to draw liquid from the level of the connection of the conduit to the tank, a motor connected to drive said pump, a control housing having an inlet chamber communicating with the outlet of said pump, a check valve arranged to close toward the outlet of the pump under the influence of back pressure in said chamber, a flow port formed in a wall of said housing and opening from said inlet chamber, means defining a flow passage connected to said housing and surrounding the outer side of said flow port, a control member having a head exposed on its outer side to said flow passage and a stem extending through said flow port, reducing the effective area of the inner side of the head which is exposed to pressure in said inlet chamber, said head on said control member being movable into substantial closing relation to said flow port, an electric switch mounted adjacent said control member and electrically connected to said motor to control the motor, means mechanically connecting said switch to said control member to open said switch in the fully extended position of said stem with said head closed in relation to said port and also in a fully retracted position of said stem with said head at a widely opened position relative to said port, means biasing said control member toward said widely opened retracted position of said head, said biasing means being of insufficient strength to fully overcome the force differential on the outer and inner sides of said head when said chamber and said flow passage are subjected to liquid pressure created by said pump in said system, said mechanical connecting means being arranged to close said switch at intermediate positions of said control member between closed and widely opened positions of said head, and means preventing the closing of said check valve when said control member is in said fully retracted position, at least part of the liquid connection to said outlet valve being located above the level of said flow chamber.

2. A water system as defined in claim 1 in which said control member is arranged in upright position with said stem extending through a bottom wall of said housing, and said flow passage is located over said housing.

3. A water system as defined in claim 2 in which said pump is arranged on a generally horizontal axis with its impeller in a generally vertical plane.

4. A water system as defined in claim 3 in which said mechanical connecting means includes a lever pivoted adjacent said switch and having one end arranged to actuate said switch, another end on said lever engageable with a projection on said control member to move said lever to switch open position in said fully retracted position of said stem, and a portion on said stem arranged to open said switch in the extended position of said stem and the related closed position of said head.

5. A water system as defined in claim 4 in which said means preventing the closing of said check valve comprises a mechanical link between said check valve and said control member.

6. A water system as defined in claim 5 in which said mechanical link comprises a flexible strand connected between said head of said control member and a swinging portion of said valve.

7. A water system as defined in claim 1 in which said check valve comprises a yieldably suspended closure element responsive to back pressure in said housing, and means yieldably biasing said closure element to partially open position.

8. A water system as defined in claim 7 in which said yieldable biasing means for said closure element comprises a weight carried thereby in offset relation to the suspension point of the closure to hang by gravity with the closure in partially open position.

9. A water system as defined in claim 4 in which said other end of said lever extends through a slot in said stem of said control member and the projection on the control member is formed by the upper end of the slot, the lower end of said stem constituting the portion thereof arranged to open said switch.

10. A water system as defined in claim 4 in which there is a flexible diaphragm having a reverse fold therein, the outer edge of the diaphragm being sealed to said housing and an inner edge of said diaphragm being sealed to said stem within said housing to seal said stem to the housing.

11. A water system as defined in claim 1 in which said inlet to said pump is located at a level not substantially above the level of the connection to said conduit to said tank.

12. A control system for a pump having an outlet and a motor connected to drive the pump comprising, a control housing having an inlet chamber communicating with the outlet of said pump, a check valve arranged to close over the outlet of the pump under the influence of back pressure in said chamber, a flow port formed in a wall of said housing and opening from said inlet chamber, means defining a flow passage connected to said housing and surrounding the outer side of said flow port, a control member in said flow passage arranged in opposed relation to said flow port and exposed therethrough to said inlet chamber, said control member having a larger area exposed to pressure in said flow passage than the opposing area exposed to pressure in said inlet chamber, an electric switch mounted adjacent said control member and electrically connected to said motor to control the motor, means mechanically connecting said switch to said control member to open said switch in fully extended position of said control member into closed relation to said port and also in fully retracted position in widely opened position relative to said port, means biasing said control member toward said widely opened position, said biasing means being of insufficient strength to overcome the force differential on the outer and inner sides of said control member when said chamber and said flow passage are filled with liquid under pressure, said mechanical connecting means being arranged to close said switch at intermediate positions of said control member between closed and widely opened positions relative to said flow port, and means preventing the closing of said check valve when said control member is in said fully retracted position.

13. A control for a pump as defined in claim 12 in which said control member has a head exposed to the pressure in said flow passage and a stem extending through said flow port and slidably and sealingly through a wall of said inlet chamber, said switch being located externally of said housing in coacting relation to said stem.

14. A control for a pump as defined in claim 13 in which there are means forming a pressure bleed passage between said flow passage and said inlet chamber when said head is closed over said port.

15. A control for a pump as defined in claim 14 in which there is an annular ring with a radially inwardly tapering edge disposed between said head and the edge of said port which forms one edge of said annular passage when said control member is retracted and which forms the final closure around said head, said tapering edge being inclined axially and radially toward flow directed radially outwardly under said head.

16. A control for a pump as defined in claim 15 in which said annular ring has its outer edge secured between said housing and said means defining said flow passage, with said tapering edge seating against the underside of said head.

17. A control for a pump as defined in claim 13 in which there is an annular guide secured to said housing within said inlet chamber and projecting inwardly thereof around said stem, and a flexible diaphragm with an annular reverse bend therein, said diaphragm having its outer edge secured between said housing and said guide and an inner edge secured to said stem.

18. A control for a pump as defined in claim 13 in which a spring compressed between said guide and said head forms the biasing means for said control member.

19. A control for a pump as defined in claim 13 in which said means preventing the closing of said check valve comprises a mechanical link between said check valve and said control member.

20. A control for a pump as defined in claim 13 in which said mechanical connecting means includes a lever pivoted adjacent said switch and having one end arranged to actuate said switch, another end on said lever engageable with a projection on said control member to move said lever to switch open position in said fully retracted position of said stem, and a portion on said stem arranged to open said switch in the extended position of said stem and the related closed position of said head.

*21. A control system for a pump having an outlet and a motor connected to drive the pump comprising,*

*means forming an inlet chamber communicating with the outlet of the pump,*

*a check valve located between said inlet chamber and said pump,*

*means forming a flow passage communicating with said inlet chamber through a flow port,*

*a control member positioned in said flow passage in opposed relation to said flow port,*

*said control member having a larger area exposed to pressure in said flow passage than the opposed area exposed to pressure in said inlet chamber through said flow port,*

*electric switch means connected to control said motor,*

*means mechanically connecting said switch to said control member to open said switch means when said control member is in a first extreme position in closing relation to said port and also when said control member is in a second and opposite extreme position in spaced relation to said port,*

*and means biasing said control member toward said second extreme position,*

*said biasing means being of insufficient strength to overcome the force differential created on opposite sides of said control member by liquid being delivered by said pump through said inlet chamber, flow passage and flow chamber,*

*said mechanical connecting means being arranged to close said switch means at positions of said control member intermediate of said first and second extreme positions.*

*22. A control system as defined in claim 21 in which said means mechanically connecting said control member to said switch means includes:*

*a stem-like extension on the control member extending through said port with an end extending in sliding and sealed relation through a wall of said inlet chamber.*

*23. A control system as defined in claim 22 in which said mechanical connecting means includes a pivotally mounted lever having one end positioned to actuate said switch means,*

*a lever actuating surface on said stem-like extension arranged to move the other end of said lever to open said switch means in the second extreme position of said control member,*

*and a second actuating surface on said stem-like extension arranged to open said switch means in the first extreme position of said control member.*

References Cited

The following references, cited by the Examiner, are of record in the patented file of this patent or the original patent.

UNITED STATES PATENTS

| | | | |
|---|---|---|---|
| 1,952,265 | 3/1934 | Leland. | |
| 1,973,842 | 9/1934 | Broderick. | |
| 2,020,485 | 11/1935 | Van Valkenburg et al. | 103—25 |
| 2,244,373 | 6/1941 | Powers | 200—81.9 |
| 2,485,074 | 10/1949 | Stevenson. | |
| 2,616,009 | 10/1952 | Roesek | 200—160 |
| 2,630,069 | 3/1953 | Harris. | |
| 2,761,389 | 7/1956 | Turner. | |
| 3,278,704 | 10/1966 | Smith | 103—25 |
| 3,299,817 | 1/1967 | Walters et al. | |
| 3,283,094 | 11/1966 | Lung | 200—81.9 |

WILLIAM L. FREEH, Primary Examiner.

U.S. Cl. X.R.

200—81.9, 82, 160